(12) United States Patent
Mandava et al.

(10) Patent No.: US 8,058,438 B2
(45) Date of Patent: Nov. 15, 2011

(54) ESZOPICLONE PROCESS

(75) Inventors: Venkata Naga Brahmeswara Rao Mandava, Hyderabad (IN); Sreenadhacharyulu Kandala, Hyderabad (IN); Mukunda Reddy Jambula, Mahaboob Nagar (IN); Raveendra Reddy Chinta, Chittoor (IN)

(73) Assignees: Dr. Reddy's Laboratories Limited, Hyderabad, Andhra Pradesh (IN); Dr. Reddy's Laboratories, Inc.,, Bridgewater, NJ (US)

( * ) Notice: Subject to any disclaimer, the term of this patent is extended or adjusted under 35 U.S.C. 154(b) by 342 days.

(21) Appl. No.: 12/339,253

(22) Filed: Dec. 19, 2008

(65) Prior Publication Data

US 2009/0099359 A1    Apr. 16, 2009

Related U.S. Application Data

(62) Division of application No. 11/469,920, filed on Sep. 5, 2006, now Pat. No. 7,476,737.

(60) Provisional application No. 60/788,276, filed on Mar. 31, 2006, provisional application No. 60/746,394, filed on May 4, 2006.

(30) Foreign Application Priority Data

Sep. 5, 2005  (IN) .......................... 1241/CHE/2005
Dec. 9, 2005  (IN) .......................... 1806/CHE/2005
Jun. 22, 2006 (IN) .......................... 1064/CHE/2006

(51) Int. Cl.
C07D 487/02    (2006.01)
(52) U.S. Cl. ........................................ 544/350; 544/336
(58) Field of Classification Search .................. 544/336, 544/339, 350
See application file for complete search history.

(56) References Cited

U.S. PATENT DOCUMENTS

| 3,862,149 | A | 1/1975 | Cotrel et al. |
| 6,339,086 | B1 | 1/2002 | Jerussi et al. |
| 6,444,673 | B1 | 9/2002 | Cotrel et al. |
| 7,476,737 | B2 * | 1/2009 | Mandava et al. ............... 544/350 |
| 7,772,396 | B2 * | 8/2010 | Bleda et al. ................... 544/350 |
| 7,786,304 | B2 * | 8/2010 | Sawant et al. ................. 544/350 |
| 2005/0043311 | A1 | 2/2005 | Cotrel et al. |
| 2007/0203145 | A1 | 8/2007 | Zhu |

FOREIGN PATENT DOCUMENTS

| WO | 00/69442 A1 | 11/2000 |
| WO | 2007/083188 A2 | 7/2007 |

* cited by examiner

*Primary Examiner* — Golam M M Shameem
(74) *Attorney, Agent, or Firm* — Robert A. Franks; Balaram Gupta; Thomas C. McKenzie

(57) ABSTRACT

Eszopiclone is prepared by reacting zopiclone with an enatiomerically pure di-p-toluoyl tartaric acid, recovering a solid salt, and reacting a solid salt with a base. Zopiclone is prepared by reacting 6-(5-chloropyrid-2-yl)-5-hydroxy-7-oxo-5,6-dihydropyrrolo[3,4-b]-pyrazine with 1-chlorocarbonyl-4-methylpiperazine hydrochloride.

21 Claims, 2 Drawing Sheets

Formula II

Formula IIa

Formula I

ESZOPICLONE PROCESS

INTRODUCTION TO THE INVENTION

The present invention relates to a process for the preparation of eszopiclone and intermediates thereof.

Eszopiclone is chemically described as (+)-(5S)-6-(chloropyridin-2-yl)-7-oxo-6,7-dihydro-5H-pyrrolo[3,4-b]pyrazin-5-yl4-methyl-piperazine-1-carboxylate and has the structural Formula I.

Formula I

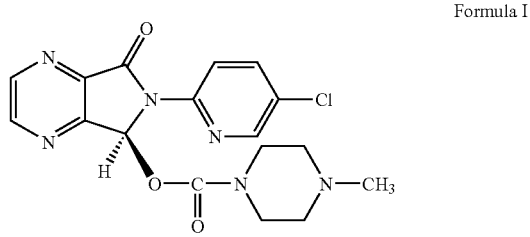

Eszopiclone is non-benzodiazepine hypnotic useful in the treatment of insomnia and is the more active dextrorotatory isomer of zopiclone. It is commercially available under the brand LUNESTA™ as tablets containing 1 mg, 2 mg, or 3 mg of eszopiclone.

U.S. Pat. No. 3,862,149 discloses a process for the preparation of zopiclone, which involves reacting the compound 6-(5-chloropyrid-2-yl)-5-hydroxy-7-oxo-5,6-dihydropyrrolo[3,4-b]pyrazine with the compound 1-chlorocarbonyl-4-methylpiperazine in presence of sodium hydride, employing dimethylformamide as the solvent.

U.S. Pat. No. 6,444,673 discloses the separation of the eszopiclone from racemic zopiclone by several methods, such as chiral-phase chromatography, resolution of an optically active salt, stereo-selective enzymatic catalysis by means of an appropriate microorganism, and asymmetric synthesis. Pharmaceutical compositions of eszopiclone are also described.

U.S. Pat. No. 6,339,086 discloses the resolution of racemic N-desmethylzopiclone using methods such as chiral chromatography, the use of one or more chiral acids, i.e. malic acid, mandelic acid, and dibenzoyltartaric acid for the preparation of optically pure (+)-N-desmethylzopiclone, and optically pure (−)-N-desmethylzopiclone.

The zopiclone preparation process suffers from serious disadvantages such as use of 1-chlorocarbonyl-4-methylpiperazine, which is unstable under ambient conditions, and moreover is commercially unavailable. The process also uses an excess of solvents, which leads to poor yields of the final compound, and increases the time for completion of the reaction. The final product in the process was purified using column chromatography, and a mixture of solvents for recrystallization. These solvents are difficult to recover, which makes the process unsuitable for use on a commercial scale.

The present invention addresses these and other problems and provides a process that is simple, efficient, inexpensive, ecofriendly, robust, and readily scaleable.

SUMMARY OF THE INVENTION

The present invention relates to a process for the preparation of eszopiclone and intermediates thereof.

In one aspect, the present invention relates to a process for the preparation of eszopiclone of Formula I, which process comprises:

a) reacting zopiclone with an enantiomerically pure di-p-toluoyl tartaric acid; and b) recovering a solid salt.

The process can further comprise reacting the solid salt with a base to form eszopiclone.

In another aspect, the present invention relates to a process for the preparation of the zopiclone compound of Formula II, which is an intermediate in the synthesis of eszopiclone of Formula I. An embodiment of the process comprises reacting 6-(5-chloropyrid-2-yl)-5-hydroxy-7-oxo-5,6-dihydropyrrolo[3,4-b]pyrazine of Formula IV with 1-chlorocarbonyl-4-methylpiperazine hydrochloride of Formula III, to form zopiclone.

DETAILED DESCRIPTION OF THE INVENTION

Figure 1:
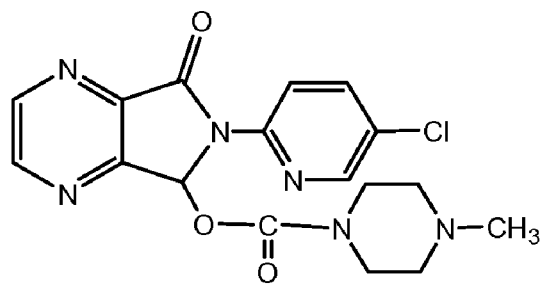
FIG. 1 is a schematic representation of a process for preparing the compound of Formula I.
Figure 1:
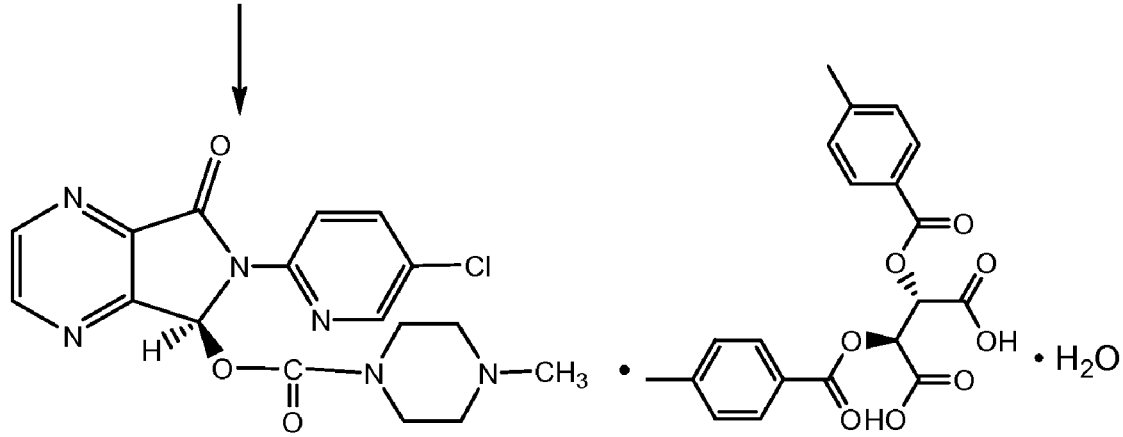
Figure 1:
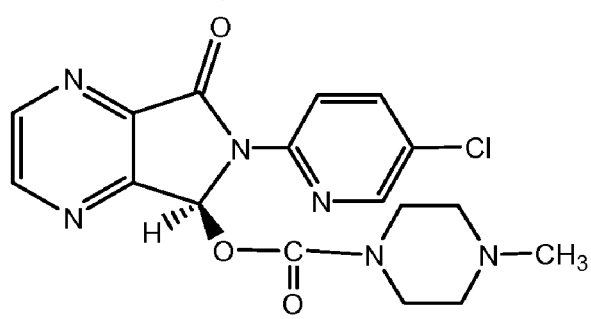
Figure 2:
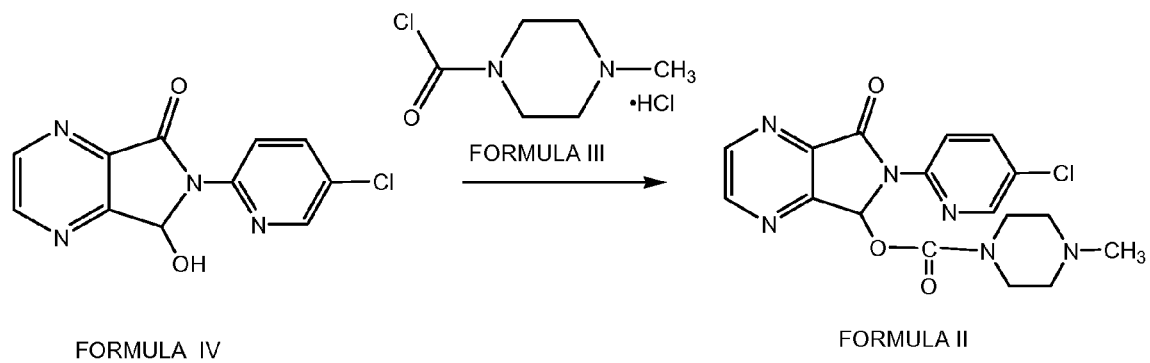
FIG. 2 is a schematic representation of a process for preparing the compound of Formula II.

The present invention relates to a process for the preparation of eszopiclone and intermediates thereof.

In one aspect, the present invention relates to a process for the preparation of eszopiclone compound of Formula I which process comprises:

a) reacting zopiclone compound of Formula II with an enantiomerically pure di-p-toluoyl tartaric acid;

b) recovering a solid product comprising the compound of Formula IIa; and c) reacting the solid product comprising the compound of Formula IIa with a base to form eszopiclone.

Step a) involves reacting zopiclone with a di-p-toluoyl tartaric acid in a suitable solvent.

An example of a suitable acid is di-p-toluoyl-D-tartaric acid, including hydrated forms of the acid.

Suitable solvents that can be used in step a) include but are not limited to: ketonic solvents such as acetone, ethyl methyl ketone, methyl isobutyl ketone and the like; esters such as ethyl acetate, n-propyl acetate, n-butyl acetate, tertiary butyl acetate and the like; nitrile solvents such as acetonitrile, propionitrile and the like; aprotic polar solvents such as N,N-dimethylformamide, dimethylsulfoxide, N,N-dimethylacetamide and the like; or mixtures thereof or their combination with water in various proportions.

Suitably, the molar ratio of enantiomerically pure acid to the eszopiclone used in the reaction can range from about 1:1-4, or about 1:1-2, or about 1:0.9.

Suitable temperatures for conducting the reaction include about 20° C. to 100° C., or about 50° C. to 60° C. The reaction can be conducted as long as required for the completion of the reaction, about 30 minutes to about 5 hours frequently being required.

Step b) involves recovering a solid product comprising the compound of Formula IIa.

After completion of the reaction, the product is isolated by forcible or spontaneous crystallization. Spontaneous crystallization refers to crystallization without the help of an external aid and forcible crystallization refers to crystallization with the help of an external aid.

Forcible crystallization may be initiated by methods known in the art such as cooling, seeding, partial removal of the solvent from the reaction solution by adding an anti-solvent to the solution, or a combination thereof.

The solid product thus obtained is recovered from the reaction mixture by suitable techniques such as decantation, filtration by gravity or by suction, centrifugation, and the like. The crystals so isolated can carry a small proportion of occluded mother liquor containing a higher percentage of impurities. If desired, the crystals can be washed on the filter with a solvent to wash out the mother liquor.

The wet cake obtained in step b) may optionally be further dried. Drying can be suitably carried out in a tray dryer, vacuum oven, air oven, fluidized bed drier, spin flash dryer, flash dryer and the like. The drying can be carried out at temperatures of about 35° C. to about 70° C. for any desired time period to achieve a desired result, times from about 1 to 20 hours frequently being suitable.

Step c) involves reacting the solid product comprising compound of Formula IIa with a base in a suitable solvent to form eszopiclone.

Suitable bases that can used in the reaction include but are not limited to: alkali metal hydroxides such as lithium hydroxide, sodium hydroxide, potassium hydroxide and the like; carbonates of alkali metals such as sodium carbonate, potassium carbonate and the like; bicarbonates of alkali metals such as sodium bicarbonate, potassium bicarbonate, and the like; ammonia; and mixtures thereof. These bases can be used in the form of solids or in the form of aqueous solutions Suitably, aqueous solutions containing about 5% to 50%, or about 10% to 20%, (w/v) of the corresponding inorganic base can be used.

Suitable solvents which can be used in the reaction include, but are not limited to: esters such as ethyl acetate, n-propyl acetate, n-butyl acetate, t-butyl acetate and the like; hydrocarbons such as toluene, xylene, n-hexane, n-heptane, cyclohexane and the like; ether solvents such as diethyl ether, diisopropyl ether, methyl tertiary butyl ether and the like; and mixtures thereof.

Suitably, reaction mixture pH values may range from about 7 to about 11, or about 7 to 9. Suitable temperatures for conducting the reaction can range from about 10° C. to about 50° C., or about 25 to 35° C.

After reaction completion, organic layer containing the free base is separated and may be proceeded to further processing directly or it can be concentrated to form a residue.

The residue thus obtained can optionally be further purified by crystallizing from a suitable solvent.

Suitable solvents that can be used in the purification process include but are not limited to: ketonic solvents such as acetone, ethyl methyl ketone, methyl isobutyl ketone and the like; esters such as ethyl acetate, n-propyl acetate, n-butyl acetate, tertiary butyl acetate and the like; and nitrile solvents such as acetonitrile, propionitrile and the like.

In another aspect of the present invention, there is provided a process for the preparation of zopiclone of Formula II, comprising: reacting the compound 6-(5-chloropyrid-2-yl)-5-hydroxy-7-oxo-5,6-dihydropyrrolo[3,4-b] pyrazine of Formula IV

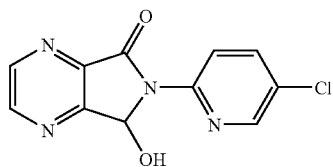

Formula IV with 1-chlorocarbonyl-4-methylpiperazine hydrochloride of Formula III

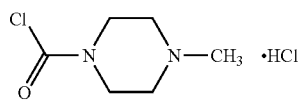

Formula III to afford zopiclone of Formula II.

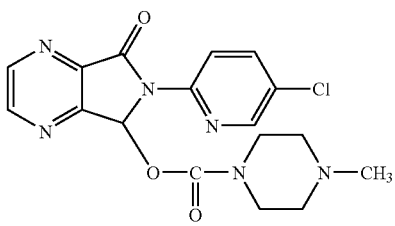

(II)

The reaction of 6-(5-chloropyrid-2-yl)-5-hydroxy-7-oxo-5,6-dihydropyrrolo[3,4-b]pyrazine compound of Formula IV with 1-chlorocarbonyl-4-methylpiperazine hydrochloride compound of Formula III occurs in the presence of a suitable base and a suitable organic solvent, and optionally a suitable catalyst being present, to afford zopiclone of Formula II.

Suitable bases include but are not limited to: organic bases such as methylamine, dimethylamine, triethylamine, di-isopropylamine N,N-di-isopropylethylamine, butylamine and the like; inorganic bases including alkali metal compounds such as sodium hydride and potassium hydride, sodium hydroxide, potassium hydroxide, sodium methoxide, potassium methoxide, sodium carbonate, sodium bicarbonate, potassium carbonate, potassium bicarbonate and the like; or mixtures thereof.

Suitable catalysts include but are not limited to quaternary amine salts, such as those having the formula $R^1R^2R^3R^4NX$, where individual R groups are the same or different hydrocarbon groups and X is an anion. Representative useful quaternary ammonium salts include tetrabutylammonium bromide, tetrabutylammonium chloride, tetrabutylammonium fluoride trihydrate, tetrabutylammonium hydrogen sulfate, tetrabutylammonium iodide, tetrabutylammonium thiocyanate, tetrabutylammonium tetrafluoroborate, benzyltributylammonium chloride, benzyltriethylammonium chloride, benzyltrimethylammonium bromide, benzyltrimethylammonium chloride, hexadecyltrimethylammonium bromide, hexadecyltrimethylammonium chloride, hexadecyltrimethylammonium hydrogen sulfate, methyltrioctadecylammonium bromide, and the like.

Suitable organic solvents include but are not limited to: ketone solvents such as acetone, methyl ethyl ketone, methyl isobutyl ketone, n-butanone, tertiary butyl ketone and the like; nitrile solvents such as acetonitrile, propionitrile and the like; halogenated solvents such as dichloromethane, ethylene dichloride, chloroform and the like; esters such as ethyl acetate, n-propylacetate, isopropyl acetate, tertiary butyl acetate and the like; aprotic polar solvents such as N,N-dimethylformamide, dimethylsulfoxide, N,N-dimethylacetamide and the like; ethers such as dimethylether, diethyl ether, di-isopropylether, methyl tertiary butyl ether, tetrahydrofuran, 1,4-dioxane, and the like; hydrocarbon solvents such as toluene, xylene, n-hexane, n-heptane, cyclohexane and the like; and mixtures thereof or their combinations with water in various proportions without limitation.

The reaction temperatures can range from about −80° C. to about 50° C.

Crude zopiclone can be recrystallized to afford the zopiclone compound of Formula II in a more pure form using suitable organic solvent(s) at suitable temperature(s).

Suitable organic solvents include but are not limited to: alcohols such as methanol, ethanol, isopropyl alcohol, n-butanol and the like; ketonic solvents such as acetone, ethyl methyl ketone, methyl isobutyl ketone and the like; esters such as ethyl acetate, n-propyl acetate, isopropyl acetate, n-butyl acetate, t-butyl acetate and the like; nitrile solvents such as acetonitrile, propionitrile and the like; halogenated solvents such as dichloromethane, ethylene dichloride, chloroform and the like; ethers such as dimethylether, diethyl ether, diisopropyl ether, methyl tertiary butyl ether tetrahydrofuran, 1,4-dioxane and the like; hydrocarbons solvents such as toluene, xylene, n-hexane, n-heptane, cyclohexane and the like; and mixtures thereof or their combinations with water in various proportions without limitation.

Suitable temperatures for recrystallisation can range from about −15° C. to about 30° C.

The compound of Formula III is highly stable and commercially useful and its corresponding free base form is unstable at ambient conditions. By using the compound of Formula III, the yield and purity of the final compound eszopiclone are made substantially higher.

The compound of Formula II is useful as an intermediate in the synthesis of eszopiclone of Formula I, and frequently has a purity by high performance liquid chromatography ("HPLC") that is greater than or equal to 99.8 area-%.

The process according to the present invention preferably yields substantially pure eszopiclone. Thus, the ratio of S-zopiclone:R-zopiclone as prepared by the present invention can be at least about 99.8% as determined by chiral HPLC.

The proportion of eszopiclone realized by the process of the present invention can be increased by effecting one or more, for example two or three, recrystallizations resulting in eszopiclone with an enantiomeric purity of at least 99.5% and is particularly substantially free of the levorotatory form R-zopiclone or (−)-zopiclone and other process related impurities. Enantiomeric enrichment can be obtained by simple recrystallisation using solvents like acetonitrile.

Thus, an aspect of the present invention is directed to a resolution process for preparation of eszopiclone with low residual solvent levels.

In yet another aspect, the present invention encompasses pharmaceutical compositions comprising eszopiclone of Formula I made by the process of the present invention and at least one pharmaceutically acceptable carrier.

The drug substance can be formulated as solid compositions for oral administration, such as tablets, pills, powders or granules. In these compositions, the active product according to the invention is mixed with one or more inert diluents such as sucrose, lactose, mannitol or starch. These compositions can also comprise substances other than diluents, e.g. a lubricant such as magnesium stearate.

The drug substance can be formulated as liquid compositions for oral administration, such as solutions, suspensions, syrups, elixirs and pharmaceutically acceptable emulsions, containing inert diluents such as water or liquid paraffin. These compositions can also comprise substances other than diluents, e.g. wetting, sweetening or flavouring agents.

The compositions for parenteral administration can be suspensions, emulsions or aqueous or non-aqueous, sterile formulations. As a solvent or vehicle, propylene glycol, polyethylene glycol, vegetable oils, especially olive oil, and injectable organic esters, e.g. ethyl oleate, may be employed. These compositions can contain adjuvants, especially wetting, emulsifying and dispersing agents. The sterilization may be carried out in several ways, e.g. using a bacteriological filter, by incorporating sterilizing agents in the composition, by irradiation, or by heating. They may be prepared in the form of sterile solid compositions, which can be dissolved or dispersed at the time of use in sterile water or any other sterile injectable medium.

Pharmaceutically acceptable carriers that can be used in the present invention are but not limited to diluents such as starch, pregelatinized starch, lactose, powdered cellulose, microcrystalline cellulose, dicalcium phosphate, tricalcium phosphate, mannitol, sorbitol, sugar and the like; binders such as acacia, guar gum, tragacanth, gelatin, polyvinyl pyrrolidone, hydroxypropyl cellulose, hydroxypropyl methylcellulose, pregelatinized starch and the like; disintegrants such as starch, sodium starch glycolate, pregelatinized starch, crospovidone, croscarmellose sodium, colloidal silicon dioxide and the like; lubricants such as stearic acid, magnesium stearate, zinc stearate and the like; glidants such as colloidal silicon dioxide and the like; solubility or wetting enhancers such as anionic or cationic or neutral surfactants, complex forming agents such as various grades of cyclodextrins, resins; release rate controlling agents such as hydroxypropyl cellulose, hydroxymethyl cellulose, hydroxypropyl methylcellulose, ethyl cellulose, methyl cellulose, various grades of methyl methacrylates, waxes and the like. Other pharmaceutically acceptable excipients that are of use include but not limited to film formers, plasticizers, colorants, flavoring agents, sweeteners, viscosity enhancers, preservatives, antioxidants and the like.

The process of the present invention is efficient, cost effective, ecofriendly, reproducible, scalable, robust and commercially feasible. The process of the present invention produces the desired compound eszopiclone with high yield and purity.

Certain specific aspects of the present invention will be explained in more detail with reference to the following examples, which are provided by way of illustration only and should not be construed as limiting the scope of the invention in any manner.

EXAMPLE 1

Preparation of (+)-(5S)-6-(chloropyridin-2-yl)-7-oxo-6,7-dihydro-5H-pyrrolo[3,4-B]pyrazin-5-yl-4-methyl-piperazine-1-carboxylate (Formula I)

65 ml of acetonitrile and 5 g of zopiclone of Formula II were charged into a clean and dry round bottom flask followed by heating to about 50° C. 5.2 g of di-p-toluoyl-D-tartaric acid monohydrate was charged followed by stirring for about 15 minutes and the resultant reaction mass was further heated to about 75° C. The reaction mass was stirred for about 10 minutes followed by cooling to about 30° C. The reaction suspension was stirred for about 30 minutes followed by filtration of the separated solid. The solid was washed with 5 ml of acetonitrile to afford 5.2 g of a wet di-p-toluoyl-D-tartaric acid salt of eszopiclone of Formula IIa.

5 g of the above wet di-para-toluoyl-D-tartaric acid salt of eszopiclone of Formula IIa, 20 ml of water and 50 ml dichloromethane were charged in a clean and dry 4-neck round bottom flask accompanied by mixing, followed by cooling to about 5° C. The pH of the solution was adjusted to about 8.5 by the addition of 13 ml of 10% aqueous sodium carbonate solution over a period of about 15 minutes. The resultant suspension was stirred for about 30 minutes followed by separation of organic and aqueous phases. The aqueous phase was extracted with 10 ml of dichloromethane followed by separation of organic and aqueous phases. Both of the organic phases were combined and distilled completely at about 36° C. under vacuum to afford 2.4 g of the free base title compound.

2.4 g of above obtained free base and 24 ml of acetonitrile were charged in a clean and dry 4 neck round bottom flask followed by heating to about 75° C. The solution was stirred for about 5 minutes followed by cooling to about 30° C. for about 30 minutes. Separated solid was filtered and was washed with 2.4 ml of acetonitrile followed by drying the solid at about 45° C. to afford 1.3 g of the title compound.

Purity: 99.98 area-% by chiral HPLC.
Specific optical rotation (SOR): $[\beta]^{20}{}_D$=(+) 134.6° (c=1%, acetone).
Melting point: 203-206° C.

EXAMPLE 2

Process for the Preparation of (±)-6-(5-chloro-2-pyridinyl)-6,7-dihydro-7-oxo-5H-pyrrolo-[3,4B]pyrazin-5-yl-4-methylpiperazine-1-carboxylate (Zopiclone) (Formula II)

200 ml of methyl isobutyl ketone and 20 g of 6-(5-chloropyrid-2-yl)-5-hydroxy-7-oxo-5,6-dihydropyrrolo[3,4-b]pyrazine of Formula IV were charged into a clean and dry round 4-neck round bottom flask followed by stirring for about 10 minutes. 48 g of potassium carbonate was charged followed by stirring for about 10 minutes. 23 g of 1-chlorocarbonyl-4-methylpiperazine hydrochloride of Formula III was charged followed by charging of 2 g of tetrabutyl ammonium bromide. The resultant reaction mass was stirred at about 25-35° C. for about 18 hours followed by cooling to about 5° C. The reaction was stirred at about 5° C. for about 10 minutes followed by filtration of the solid separated. The solid was washed with 20 ml of methyl isobutyl ketone and the wet solid was charged into a round bottom flask containing 600 ml of precooled water. The reaction suspension was stirred at about 5° C. for about 35 minutes followed by filtration of the solid. The solid was washed with 160 ml of water followed by charging of wet solid into a clean and dry round bottom flask. 560 ml of dichloromethane and 80 ml of water were charged followed by cooling to about 5° C. The pH of the resultant suspension was adjusted to about 12.5 by the addition of 1 ml of 2N sodium hydroxide solution followed by stirring for about 25 minutes. The organic and aqueous layers were separated and the organic layer was washed with 400 ml of water. Organic and aqueous layers were separated and the organic layer was washed with 100 ml of water followed by separation of organic and aqueous layers. The organic layer was distilled completely at about 40° C. and the solid residue was taken into clean and dry round bottom flask. 200 ml of ethyl acetate was charged to the solid followed by heating to about 70° C. for about 25 minutes. 2 g of charcoal carbon was charged followed by stirring for about 15 minutes. The suspension was filtered though celite and the celite was washed with 20 ml of preheated ethyl acetate. The filtrate was cooled to about 2° C. for about 20 minutes followed by filtration of separated solid and the solid was washed with 20 ml of precooled ethyl acetate. The solid obtained was dried at about 65° C. for about 2 hours to afford 15 g of the title compound of Formula II with a purity of 99.65 area-% by HPLC.

EXAMPLE 3

Alternate Process for the Preparation of (±)-6-(5-chloro-2-pyridinyl)-6,7-dihydro-7-oxo-5H-pyrrolo-[3,4B]pyrazin-5-yl-4-methylpiperazine-1-carboxylate (Zopiclone) (Formula II)

125 ml of N,N-dimethylformamide and 9.2 g of sodium hydride were charged in a clean and dry 4-neck round bottom flask at about −10° C. followed by stirring for about 20 minutes. 25 g of 6-(5-chloropyrid-2-yl)-5-hydroxy-7-oxo-5,6-dihydropyrrolo[3,4-b]pyrazine of Formula IV was charged followed by stirring for about 20 minutes. 29 g of 1-chlorocarbonyl-4-methylpiperazine hydrochloride of Formula III was added in three lots to the above reaction mixture followed by stirring at about −10° C. for about 1 hour and then quenching the reaction mass by adding the reaction mass to 1500 ml of water and further stirring for about 15 minutes. The separated solid was filtered and the solid was washed with 250 ml of water. The obtained solid was dissolved in a mixture of 700 ml of dichloromethane and 100 ml of water. The resultant suspension was cooled to about 2° C. and the pH was adjusted to about 12.4 with 50 ml of 2N aqueous sodium hydroxide solution followed by stirring for about 15 minutes. The organic and aqueous layers were separated and to the organic layer 100 ml of water was charged. The pH of the reaction suspension was adjusted to 12.6 with 25 ml of 2N aqueous sodium hydroxide solution followed by stirring for about 15 minutes. Organic and aqueous layers were separated and the organic layer was washed with 2×100 ml of water followed by separation of organic and aqueous layers.

Organic layer was distilled to dryness at about 42° C. under vacuum to afford a crude residue of title compound. To the residue 300 ml of ethyl acetate was charged followed by heating to about 75° C. 2.5 g of charcoal carbon was charged and the resultant reaction suspension was stirred for about 30 minutes. The reaction suspension was filtered though celite and the celite was washed with 25 ml of ethyl acetate. The filtrate was cooled to about 5° C. followed by stirring for about 20 minutes. Separated solid was filtered and the solid was washed with 25 ml of ethyl acetate to afford 22 g of a crude form of the title compound.

EXAMPLE 4

Recrystallisation of Zopiclone (Formula II)

22 g of the crude compound of Formula II from Example 3 was slurried in 250 ml of isopropyl alcohol followed by cooling to about 0° C. for about 15 minutes. The solid was filtered and the solid was washed with 25 ml of isopropyl alcohol. The solid obtained was dried at about 50° C. to afford 17.5 g of a pure zopiclone with purity by HPLC 99.82 area-%.

EXAMPLE 5

Alternate Process for the Preparation of (±)-6-(5-chloro-2-pyridinyl)-6,7-dihydro-7-oxo-5H-pyrrolo-[3,4B]pyrazin-5-yl-4-methylpiperazine-1-carboxylate (Zopiclone) (Formula II)

125 ml of methyl isobutyl ketone and 25 g of 6-(5-chloropyrid-2-yl)-5-hydroxy-7-oxo-5,6-dihydropyrrolo[3,4-b]

pyrazine of Formula IV were charged into a clean and dry round 4-neck round bottom flask followed by stirring for about 10 minutes. 60 g of potassium carbonate was charged followed by stirring for about 10 minutes. 37.8 g of 1-chlorocarbonyl-4-methylpiperazine hydrochloride of Formula III was charged followed by charging of 0.75 g of tetrabutyl ammonium bromide. 6.25 ml of water was charged followed by stirring at about 25-35° C. for about 3 hours. 50 ml of methyl isobutyl ketone was charged followed by stirring for at about 25-35° C. for about 3 hours. After completion of the reaction, 250 ml of water was charged followed by stirring for about 45 minutes. Separated solid was filtered and the solid was washed with 50 ml of water followed by drying the solid at about 75° C. under vacuum till to get LOD (loss on drying) of about less than 2.0% w/w. to afford 30 g of title compound in crude form.

375 ml of ethyl acetate and 30 g of above obtained crude compound was charged in a clean and dry 4 neck round bottom flask followed by heating to about 75° C. 2 g of charcoal carbon was charged to the clear reaction solution followed by stirring for about 45 minutes. The reaction suspension was filtered though celite and the celite was washed with 12.5 ml of preheated ethyl acetate. The filtrate was cooled to about 0° C. and was stirred for about 30 minutes followed by filtration of separated solid and the solid was washed with 12.5 ml of precooled ethyl acetate. The solid obtained was dried at about 75° C. under vacuum for about 2 hours to afford 27 g of the title compound of Formula II with a purity of 99.45 area-% by HPLC.

We claim:

1. A process for preparing eszopiclone, comprising reacting zopiclone with an enatiomerically pure di-p-toluoyl tartaric acid, and recovering a solid salt.

2. The process of claim 1, further comprising reacting zopiclone with di-p-toluoyl-D-tartaric acid or a hydrate thereof, and recovering a solid salt.

3. The process of claim 1, wherein a molar ratio of enantiomerically pure acid to eszopiclone is about 1:1-4.

4. The process of claim 1, wherein a molar ratio of enantiomerically pure acid to eszopiclone is about 1:1-2.

5. The process of claim 1, wherein a molar ratio of enantiomerically pure acid to eszopiclone is about 1:0.9.

6. The process of claim 1, further comprising reacting a salt with a base.

7. The process of claim 6, wherein a salt is dissolved in an organic solvent, before reacting.

8. The process of claim 6, wherein an organic solvent comprises a hydrocarbon, an ester, or an ether.

9. The process of claim 6, wherein reacting with a base occurs at pH values about 7 to about 11.

10. The process of claim 6, wherein a base is provided in the form of an aqueous solution.

11. The process of claim 6, wherein a base comprises an alkali metal hydroxide, an alkali metal carbonate, or an alkali metal bicarbonate.

12. The process of claim 6, wherein a base comprises an aqueous alkali metal carbonate.

13. The process of claim 6, wherein a base comprises aqueous sodium carbonate.

14. The process of claim 7, wherein the solvent comprises an aliphatic or aromatic hydrocarbon, an esters, a halogenated solvent, or a mixture of any two or more thereof.

15. The process of claim 7, wherein the solvent comprises a halogenated solvent.

16. The process of claim 7, wherein the solvent comprises dichloromethane.

17. The process of claim 6, further comprising forming solid eszopiclone.

18. The process of claim 17, wherein forming solid eszopiclone comprises distillation of solvent, crystallization, or both.

19. The process of claim 17, wherein forming solid eszopiclone comprises crystallization from a solvent comprising a ketone, an ester, a nitrile, or a mixture of any two or more thereof.

20. The process of claim 17, wherein forming solid eszopiclone comprises crystallization from a solvent comprising acetonitrile.

21. The process of claim 17, wherein forming solid eszopiclone comprises crystallization from a solvent comprising ethyl acetate.

* * * * *